(12) United States Patent
Wong et al.

(10) Patent No.: US 7,179,007 B2
(45) Date of Patent: Feb. 20, 2007

(54) SEMI-ENCLOSED APPLICATORS FOR DISTRIBUTING A SUBSTANCE ONTO A TARGET SURFACE

(75) Inventors: Arthur Wong, West Chester, OH (US); David John Pung, Loveland, OH (US); Alejandro Cedeno, Caracas (VE); William Paul Dirksing, Cleves, OH (US); Thomas James Manske, Jr., Mason, OH (US); Dana Paul Gruenbacher, Fairfield, OH (US); Alan Edward Sherry, Cincinnati, OH (US); Kirk Wallace Lake, Cincinnati, OH (US); Jan Hendrik Maria Verbiest, Caracas (VE)

(73) Assignee: The Procter & Gamble Company, Cincinnati, OH (US)

( * ) Notice: Subject to any disclaimer, the term of this patent is extended or adjusted under 35 U.S.C. 154(b) by 771 days.

(21) Appl. No.: 10/126,900

(22) Filed: Apr. 19, 2002

(65) Prior Publication Data

US 2005/0201812 A1 Sep. 15, 2005

Related U.S. Application Data

(63) Continuation-in-part of application No. 10/089,351, filed as application No. PCT/US00/27967 on Oct. 10, 2000, now Pat. No. 7,021,848, which is a continuation-in-part of application No. 10/089,332, filed as application No. PCT/US00/27969 on Oct. 10, 2000, which is a continuation-in-part of application No. 10/089,350, filed as application No. PCT/US00/27971 on Oct. 10, 2000, now Pat. No. 6,811,338, which is a continuation-in-part of application No. 10/089,331, filed as application No. PCT/US00/27968 on Oct. 10, 2000, now Pat. No. 7,108,440, which is a continuation-in-part of application No.

(Continued)

(60) Provisional application No. 60/217,172, filed on Jul. 10, 2000, provisional application No. 60/209,062, filed on Jun. 2, 2000.

(51) Int. Cl.
*B65B 1/04* (2006.01)

(52) U.S. Cl. ...................................................... 401/201

(58) Field of Classification Search .................... 401/6, 401/7, 8, 37, 132–135, 201, 205; 604/2, 604/3, 292, 306; 15/104.94, 227; 2/158
See application file for complete search history.

(56) References Cited

U.S. PATENT DOCUMENTS 671,296 A * 4/1901 Rowand ........................ 401/7

(Continued)

FOREIGN PATENT DOCUMENTS

WO WO 01/26499 A1 4/2001

*Primary Examiner*—Steven O. Douglas
(74) *Attorney, Agent, or Firm*—Thibault Fayette; Mark A. Charles; Kim W. Zerby

(57) ABSTRACT

The present invention provides a semi-enclosed applicator for distributing a substance onto a target surface. The applicator has a first side, a second side, and an internal cavity between the first and second sides. The applicator further includes at least one opening, such that the internal cavity is externally accessible, and the applicator further comprises: (a) a material comprising absorbent and substantially non-absorbent fibers on one of the first and second sides; (b) an absorbent core on the other of the first and second sides; and (c) a substantially fluid-impervious barrier layer within the internal cavity adjacent the absorbent core. The applicator includes at least one opening, such that the internal cavity is externally accessible, and the applicator further comprises: (a) a substantially fluid-impervious barrier layer within the internal cavity adjacent one of the sides; and (b) a rupturable fluid-containing reservoir located between the barrier layer and the side.

15 Claims, 10 Drawing Sheets

Related U.S. Application Data

(63) 10/089,355, filed as application No. PCT/US00/27973 on Oct. 10, 2000, now Pat. No. 6,726,386, which is a continuation-in-part of application No. 09/969,074, filed on Oct. 2, 2001, and a continuation-in-part of application No. 09/887,407, filed on Jun. 22, 2001, now Pat. No. 6,547,468, and a continuation-in-part of application No. 09/451,536, filed on Dec. 1, 1999, now Pat. No. 6,508,602, which is a continuation-in-part of application No. 09/415,866, filed on Oct. 8, 1999, now abandoned.

U.S. PATENT DOCUMENTS

| | | | | |
|---|---|---|---|---|
| 2,790,982 | A | * | 5/1957 | Schneider ............... 401/7 |
| 4,195,634 | A | * | 4/1980 | DiSalvo et al. ............ 604/366 |
| 4,510,640 | A | * | 4/1985 | Omori ............... 15/104.002 |
| 4,543,098 | A | * | 9/1985 | Wolfe et al. ............... 604/370 |
| 5,010,617 | A | * | 4/1991 | Nelson ............... 15/227 |
| 5,050,596 | A | * | 9/1991 | Walasek et al. ............ 607/111 |
| 6,508,602 | B1 | * | 1/2003 | Gruenbacher et al. ......... 401/7 |
| 6,588,961 | B2 | * | 7/2003 | Lafosse-Marin et al. .... 401/134 |
| 6,669,387 | B2 | * | 12/2003 | Gruenbacher et al. ......... 401/7 |
| 6,726,386 | B1 | * | 4/2004 | Gruenbacher et al. ......... 401/7 |
| 6,811,338 | B1 | * | 11/2004 | Manske et al. ............... 401/7 |
| 6,968,808 | B2 | * | 11/2005 | Claire ............... 119/652 |

* cited by examiner

SEMI-ENCLOSED APPLICATORS FOR DISTRIBUTING A SUBSTANCE ONTO A TARGET SURFACE

CROSS REFERENCE TO RELATED APPLICATIONS

This application claims benefit of the following applications, which are all incorporated by reference herein: U.S. application Ser. No. 10/089,351, Mar. 27, 2002 now U.S. Pat. No. 7,021,848; U.S. application Ser. No. 10/089,332, filed Mar. 27, 2002; U.S. application Ser. No. 10/089,350, filed Mar. 27, 2002 now U.S. Pat. No. 6,811,338; U.S. application Ser. No. 10/089,331, filed Mar. 27, 2002 now U.S. Pat. No. 7,108,440; U.S. application Ser. No. 10/089,355, filed Mar. 27, 2002 now U.S. Pat. No. 6,726,386; U.S. application Ser. No. 09/969,074, filed Oct. 2, 2001; U.S. application Ser. No. 09/887,407, filed Jun. 22, 2001 now U.S. Pat. No. 6,547,468 and U.S. application Ser. No. 09/451,536, filed Dec. 1, 1999 now U.S. Pat. No. 6,508,602.

FIELD OF THE INVENTION

The present invention relates to applicators useful for distributing substances onto target surfaces and for removing soils from a target surface. The present invention also relates to such an applicator which also contains a substance for application to the surface of a target object. More particularly, the present invention relates to such applicators wherein the substance may be released from the applicator material and distributed upon the surface of the target object, then removed from the surface and absorbed by the applicator.

BACKGROUND OF THE INVENTION

In the art of dispensing, articles have been developed which are coated or impregnated with useful substances intended to be utilized when the article is contacted with a target surface. While there are advantages with having the substance present on or near the surface of such articles, there is often the drawback that the useful substance is unprotected and is subject to inadvertent contact before intended use. Inadvertent contact may lead to contamination of the substance, loss of the substance onto surfaces other than the desired target surface, and/or contamination of such other surfaces with the substance. Moreover, the use of such articles to manually apply a substance to a surface of an object frequently results in exposure of a user's hands to the substance. At the very least such a scenario results in a waste of product and is undesirable from an aesthetic standpoint and, at worst, results in excessive exposure of the user to potentially harmful, toxic, or otherwise undesirable substances.

Other common approaches involve dispensing a substance such as a cleaner or protectant from a bottle or other closed vessel onto the target surface, then utilizing a sponge, towel, brush, or other implement to distribute the product on the surface and, if desired, absorb any excess product, potentially with another implement or substrate. Such practices are commonplace with surfaces such as glass, countertops, and other kitchen and bathroom surfaces. While such practices are widely accepted, they often result in inefficient use of product and/or contact with the substances involved. Moreover, utilizing such an implement typically only provides one type of material surface for use in contacting the substance and the target surface.

Accordingly, it would be desirable to provide an applicator for applying a substance to a target surface which permits greater control by the user during the application process.

It would also be desirable to provide such an applicator which permits the user to apply a substance to a target surface with reduced messiness and waste of the substance.

It would further be desirable to provide such an applicator which provides multiple surfaces of diverse materials and/or multiple substances for use in multiple tasks.

SUMMARY OF THE INVENTION

The present invention provides a semi-enclosed applicator for distributing a substance onto a target surface and a method for making such an applicator. The applicator has a first side, a second side, and an internal cavity between the first and second sides. The applicator can have two wetting sides, two drying sides or both a wet and a drying side. The applicator further includes at least one opening, such that the internal cavity is externally accessible.

The wetting side of the applicator comprises: (a) an inner substantially fluid-impervious barrier layer; (b) an outer distribution layer and (c) optionally a rupturable fluid-containing reservoir located between the barrier layer and the distribution layer.

The drying side of the applicator comprises: (a) an inner substantially fluid-impervious barrier layer; (b) an Absorbent Core and (c) an outer fluid pervious layer All documents cited herein are, in relevant part, incorporated herein by reference; the citation of any document is not to be construed as an admission that it is prior art with respect to the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements, reference numerals with the same final two digits identify corresponding elements, and wherein:

DETAILED DESCRIPTION OF THE INVENTION

As used herein, the term "hand article, refers to a covering for the hand or portion of the hand such as a finger or thumb. The term "disposable" is used herein to describe hand articles which are not intended to be restored or reused (i.e., they are intended to be discarded after a single use or a limited number of uses, and preferably, to be recycled, composted or otherwise disposed of in an environmentally compatible manner). As used herein the term "glove" refers to a covering for the hand having separate sections for each finger. As used herein, the term "mitt" refers to a covering for the hand having an enclosure that leaves the fingers unseparated and that may include space for the thumb in the main enclosure, or provide space for the thumb in a separate enclosure for the thumb, or may not include a thumb enclosure at all. While the terms "glove" and "mitt" have been defined with respect to the human hand, similar structures could be utilized to cover or enclose other elements of human anatomy, such as foot coverings, or other items for which coverings of a particular shape are preferred. As used herein the term "extension force" refers to forces applied by hand movements to a surface to extend and/or bend that surface linearly and/or curvilinearly.

The term "semi-enclosed applicator" is intended to refer to an applicator device having at least one externally-accessible internal cavity for receiving a portion of human anatomy such as a hand or finger so that the applicator device may be used as an implement. A glove, mitt or finger mitt would be an example of such a semi-enclosed applicator in the context of the present invention.

The term "wetting side" is intended to refer to a panel of the applicator which can be used to deliver and/or apply a product to a target surface. The term "drying side" is intended to refer to a panel of the applicator which can be used to absorb a product, dry and/or buff a surface.

Applicator Construction and Operation

Figure 1:
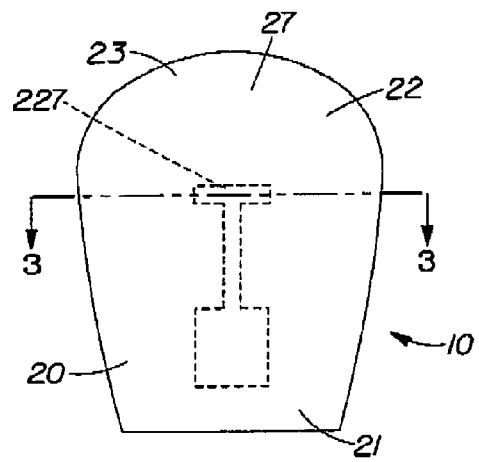
FIG. 1 is a plan view of a preferred embodiment of wetting side of a semi-enclosed applicator in accordance with the present invention, in the form of a mitt.
Figure 2:
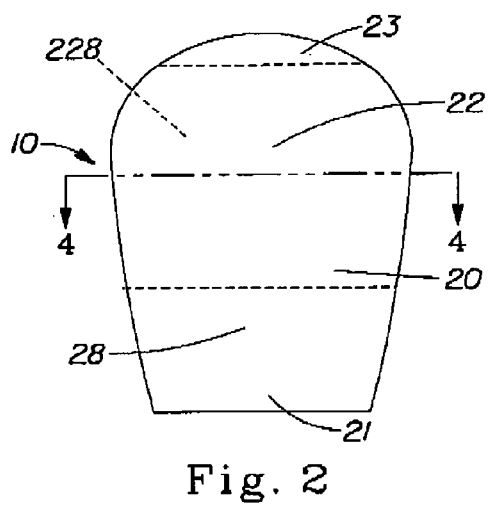
FIG. 2 is a plan view of a preferred embodiment of wet dry of a semi-enclosed applicator in accordance with the present invention, in the form of a mitt.

A representative embodiment of an example of a semi-enclosed applicator of the present invention in the form of a hand article is the disposable mitt 10 shown in FIGS. 1 and 2. which comprises a wetting side and a drying side. FIG. 1 is a plan view of the wetting side of the mitt 10 of the present invention in its flat-out state illustrating the body portion 20, cuff portion 21, central portion 22, distal portion 23, and optionally a reservoir 227. FIG. 2 is a plan view of the drying side of the mitt 10 of the present invention in its flat-out state illustrating the body portion 20, cuff portion 21, central portion 22, distal portion 23 and Absorbent Core 24. In general terms, the mitt 10 has an internal cavity which is accessible through an opening in the cuff portion and extends inwardly to the distal portion which is closed.

Figure 3:
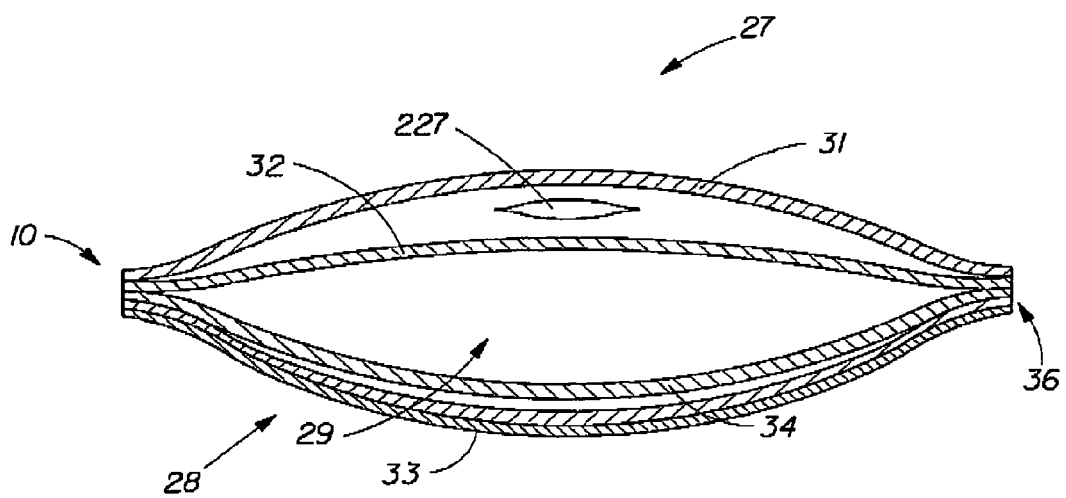
FIG. 3 is a cross-sectional view of the mitt of FIG. 1 taken along line 1—1.

FIG. 3 shows more specifically the construction details of the mitt 10 of this embodiment. The mitt 10 has a front outer surface 31, a front inner surface 32, which correspond in this embodiment to the wetting side of the mitt, a back outer surface 33, and a back inner surface 34 which correspond in this embodiment to the drying side of the mitt. The front and back inner surfaces define a hollow interior 29 into which a hand may be inserted through an opening in the cuff portion 21. The mitt 10 includes a front panel 27, which defines the front outer surface 31 of the wetting side, and a back panel 28 which defines the back outer surface 33 of the drying side. The wet and drying sides are connected along their periphery to form a seam 36. For a typical hand article, the back panel of a mitt (either wet or dry ide), is adjacent to the back of a user's hand during use and the front panel (either wet or drying side) is adjacent to the palm of a user's hand during use.

It will appear from the following description, that several types of mitts can be made depending on the intended use. A mitt may have, for example, two wetting sides, two drying sides or a wetting side and a drying side. One skilled in the art will also understand that the following wet and drying side might be used individually for applications which only require one panel. A single wet or dry panel can be provided with attachment means to secure this panel on the user's hand.

Wetting Side

In accordance with one aspect of the present invention, the mitt 10 can comprise a wetting side. By wetting side, it is meant a panel of the mitt which can be used to deliver and/or apply a product on a target surface. In one embodiment of the invention, this product is a liquid solution but other products such as gels, emulsions, creams, powders, solids or any combination thereof and more generally flowable materials are also encompassed herein.

Figure 4:
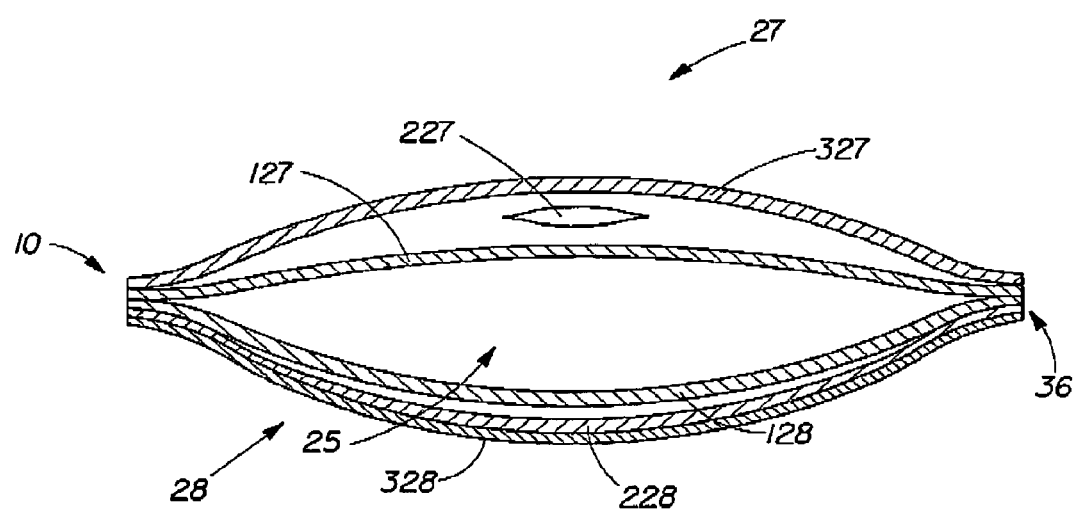
FIG. 4 is another cross-sectional view of the mitt of FIG. 1 taken along line 1—1.

In one embodiment, for which a cross-sectional view is represented in FIG. 4, a wetting side comprises at least a first layer of material 127, optionally at least a reservoir 227 for containing and dispensing a product and at least a second layer of material 337. Once a mitt is formed and the user inserts her hand in the mitt, the first layer of material will typically be in contact with the user's hand. The first layer 127 can be made of a heat sealable material, i.e. a material which is thermally bondable. The use of a heat sealable material can be particularly beneficial as it can render the manufacturing process of the mitt easier and faster and it can also contribute to reduce the manufacturing costs. In addition to these benefits, the use of a first layer of a thermally bondable material allows to add more layers of material on the top of this first layer such that these added layers can be thermally bonded to the first layer without requiring the use of an additional adhesive. One skilled in the art will understand that many "adhesive-free" processes can be used to thermally bond the layers of material. Non-limiting examples of suitable processes can be Ultrasonic bonding, Pressure bonding, Rotary Heated Crimp bonding. Ultrasonic bonding and Pressure bonding might be preferred when a thermally bondable layer is bonded to a paper-based layer. In one embodiment, at least one of the sides of a mitt 10, which can be either a wet or a drying side, comprises a thermally bondable inner layer. In this embodiment, the inner layer 127 can be used to secure both sides of the mitt together. In a preferred embodiment, both sides 27 and 28 of a mitt comprise a thermally bondable inner layer. In this embodiment, a mitt can then be formed easily by securing these two thermally bondable layers to each other by applying heat or pressure in order to form a "chassis". Additional layer of materials can be "built up" on the top of this "chassis" which also simplifies and increases the speed of the manufacturing process of the mitt. In any of the embodiments, these additional layers can be attached with an adhesive and/or can be thermally bonded to the chassis. The layers of material forming the chassis can be thermally bonded along their periphery to form the seam 36. The additional layers can also be thermally bonded along the seam 36.

When additional layers are attached to the chassis, it might be also possible to apply a layer of adhesive to these layers of material in order to form a laminate. When the reservoir 227 contains a liquid, it might also be preferred to have the first layer of the wetting side made of a fluid impervious material such that the user's hand is protected during use. Non-limiting examples of suitable fluid impervious materials which are thermally bondable can be films made of polyolefins such as Linear Low Density polyethylene, Low Density polyethylene, High Density polyethylene, polypropylene, ethyl vinyl acetate and any combination thereof. In one embodiment, a mitt comprising two sides can have two inner layer made of polyolefins. In this embodiment, these two bonded layers can be referred to a "poly to poly chassis." Additional layers can be attached to this "poly to poly chassis" either by applying a layer of adhesive, or by a thermally bonding process or any other process known in the art.

One possible use of a mitt comprising a wetting side can be for a user to apply directly or indirectly a product on a target surface or on the wetting side. The user can then contact the target surface with the outer surface 31 of the wetting side 27 in order to loosen and/or remove soil, dirt and particles. Another possible use of a mitt comprising a wetting side can be for the user to first remove particles such as dust with a cleaning sheet which in one embodiment can be a Swiffer® dry dusting sheet made by Procter and Gamble, Cincinnati, having spunlace fabric with 22% Polypropylene spunbond and 78% polyester fibers and which is described in greater details in U.S. Provisional Application Ser. No. 60/302,323 filed Jun. 29, 2001 and in U.S. Provisional Application Ser. No. 60/302,332 filed Jun. 29, 2001. Such a cleaning sheet can be integrated on the other side (dry) of the mitt 10, and a user can then apply a product on the target surface with the wetting side 27 of the mitt. Such a mitt can be particularly beneficial when the target surface needs to be "dusted" prior to applying a product such as a wax, a polish or any nourishing lotion or cream. In order to wipe a surface with the mitt, a user will have to overcome a certain amount of resistance due to the frictions between the outer surface of the wetting side and the surface to be cleaned. When the mitt is moved across the surface to be cleaned, these frictions generate a drag force. One skilled in the art will understand that in order to assure a good glide of the mitt on the surface and in order prevent the mitt from "rolling" about the user's hand, it might be beneficial that the frictions between the user's hand and the first layer of material, be greater than the frictions between the outer surface of the wetting side and the surface to be cleaned.

One way to achieve this result is to lower the frictions or resistant to the glide between the outer surface of the mitt and the surface to be cleaned. This can be done for example, by selecting a material for the second layer having a low Coefficient of Friction as measured according to ASTM D1894-90, entitled "Standard Test Method for Static and Kinetic Coefficients of Friction of Plastic Film and Sheeting." or low resistance to the glide. This can also be done by applying a product, preferably a liquid which can be for example a cleaning solution, onto the surface to be cleaned such that this applied product acts as a "lubricant."

Figure 5:
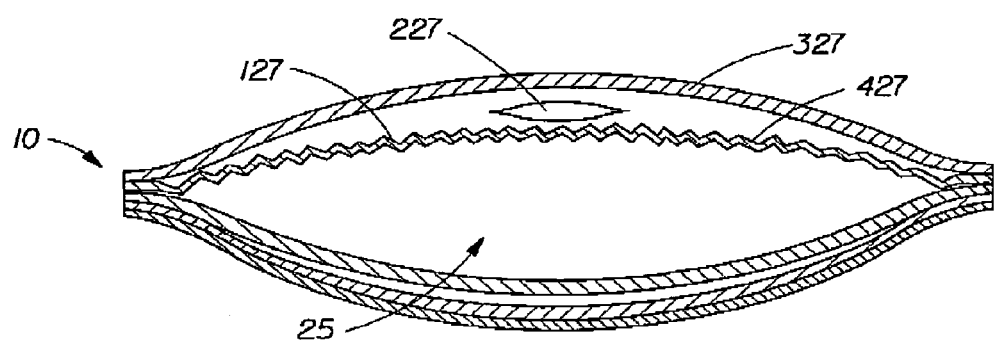
FIG. 5 is a cross-sectional view of the mitt of FIG. 1 taken along line 1—1 having "rugosities'.

Another way can be to increase the frictions between the user's hand and the first layer of material of the wetting side increase the frictions between the user's hand and the first layer of the mitt is to texture or reform the first layer of material into pleats, ribs, corrugations, and the like in any method known in the art. Such methods include but are not limited to embossing, ring-rolling, such as the one described in U.S. Pat. No. 5,167,897 issued Dec. 1, 1992, to Weber et al. and U.S. Pat. No. 5,650,214, issued Jul. 22, 1997 to Anderson et al, and incremental straining. These corrugations can also be characterized as a plurality of "rugosities." 427 FIG. 5 illustrates a cross-sectional view of an applicator similar to that of FIGS. 1 and 2, but depicting the use of an example of suitable rugosities 427 on the wetting side inner surface. In addition, the frequency of these corrugations can be controlled and designed to improve spreading of the liquid as desired. In addition to a better grip, the texture of the extensible film also provides a better aesthetic feel to the hand and can provide an elastic fit desired in a glove or mitt. One skilled in the art will understand that materials which are embossed, whether or not rendered extensible, provide improved tactile properties and greater control over the applicator in terms of contact and coefficient of friction with the hand.

Another way to increase the Coefficient of Friction is to apply an additive on at least a portion of the inner surface of the first layer of material. This additive can be a polymeric additive which is tacky at ambient temperature. Non-limiting examples of suitable additives which can have tacky properties at ambient temperature are hot melt adhesive, water based adhesive, pressure sensitive adhesive. An example of a tacky, hot melt adhesive additive and Pressure Sensitive Adhesive it is H-2031 are available from Bostik Findley, Inc. Middleton, Mass. under the reference 195-338 (hot melt) and H-2031 (pressure sensitive). Applying additives to the inner surface of the material can also be beneficial in the sense that it is possible to control the Coefficient of Friction by varying and dosing these additives.

Figure 6:
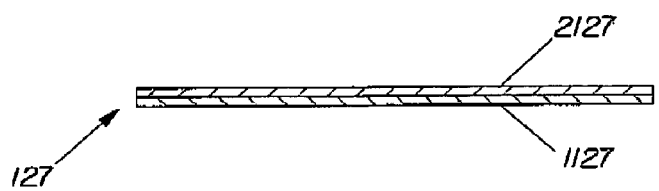
FIG. 6 is a cross-sectional view of a layer of a coextruded material.

Another way to increase the frictions between the user's hand and the inner surface of the wetting side is to make the first layer of the wetting side with a material having a high Coefficient of friction. Non-limiting examples of such materials can be films made from ethyl vinyl acetate and coextrusions of ethyl vinyl acetate/polypropylene, ethyl vinyl acetate/polyethylene, Ethylene-Methyl Acrylate and coextrusions of Ethylene-Methyl Acrylate/polyethylene, Ethylene-Methyl Acrylate/polypropylene as well as Low Density polyethylene and Low Density polyproylene, in particular metallocene catalyzed polyethylene and polypropylene with low densities. These metallocene catalyzed polyolefins can also be coextruded with polyethylene and polypropylene. In one embodiment, a material having a high Coefficient of Friction can be coextruded with another material to form this first layer. FIG. 6 shows a cross-sectional view of a suitable coextruded material of ethyl vinyl acetate 1127/polyethylene 2127. One skilled in the art will understand that it is preferable to have the surface having a high Coefficient of Friction being oriented inward, i.e. facing the user's hand.

Figure 7:
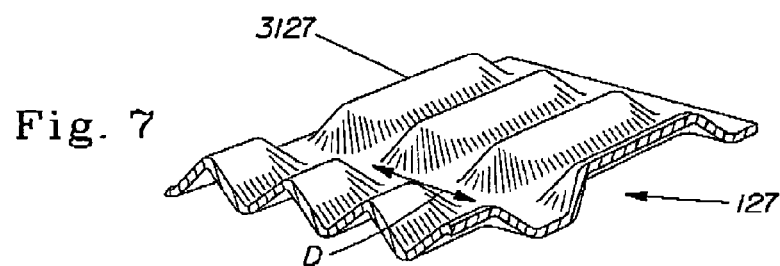
FIG. 7 is a partial perspective view of one material useful in forming the rugosities of FIG. 6.

Another way to achieve this result is to secure at least a portion of the mitt to the user's hand. One possible way to achieve this result, is to use a differentially extensible material such that at least a portion of the mitt extends and/or contracts about a wearer's hand and/or wrist without the use of traditional elastic such as natural or synthetic rubber. By the term "differentially extensible" or "differential extensibility" it is meant herein to describe that quality of extensibility wherein portions of the mitt extend or contract independently of other portions in response to varying hand sizes and motions. Preferably, this differential extensibility allows a range of hand sizes to fit comfortably within the mitt. The wetting side of a mitt 10 may be provided with differential extensibility by utilizing as the first layer of thermally bondable material, a structural elastic-like film web such as those described in commonly-assigned U.S. Pat. No. 5,518,801, issued to Chappell, et al. on May 21, 1996, and U.S. Pat. No. 5,650,214, issued Jul. 22, 1997 in the names of Anderson et al., and commonly-assigned, co-pending U.S. patent application Ser. No. 08/635,220, filed Apr. 17, 1996 in the names of Davis et al., entitled "Fitted Glove", the disclosures of each of which are hereby incorporated herein by reference. In addition, differential extensibility to fit varying sized hands comfortably can be accomplished by various elastic-like materials, composite materials that produce elastic-like characteristics and/or processes to make a material(s) more elastic-like. Non-limiting examples of suitable elastic-like materials include low density polyolefins such as low density polyethylene, linear low density polyethylene, ultra low density ethylene copolymers (copolymerized with alpha-olefins such as butene-1, octene-1, hexene-1, etc.), Affinity® polyolefin plastomers produces by Dow Chemical Company of Midland, Mich. and Exact® polyolefin plastomers produced by Exxon Chemical of Houston, Tex. As used herein, the term "elastic-like" describes the behavior f web materials such as web materials which, when subjected to an applied elongation, extend in the direction of applied elongation. Also, when the applied elongation is released the web materials return, to a substantial degree, to their untensioned condition. The term "web" as used herein refers to a sheet-like material comprising a single layer of material or a laminate of two or more layers. FIG. 7 is a perspective view of one suitable material and structural configuration which can be used for the first layer 127 of material of the wetting side, such material being consistent with the materials disclosed and claimed in the aforementioned commonly-assigned U.S. patents to Chappell, et al., and Anderson, et al. Such materials typically provide for extensibility, and (if applicable) elastic recovery, in a predominant direction illustrated via the use of the arrow labeled "D" in FIG. 7. When such a directional material is utilized in the construction of the wetting side of an applicator, the direction "D" would be oriented perpendicular to the direction in which it is desired for the rugosities to extend. Said differently, in this embodiment the direction "D" for the first layer of material of the wetting side is left to right across FIG. 5 while the rugosities 3127 extend in the direction into and out of the page.

Figure 8:
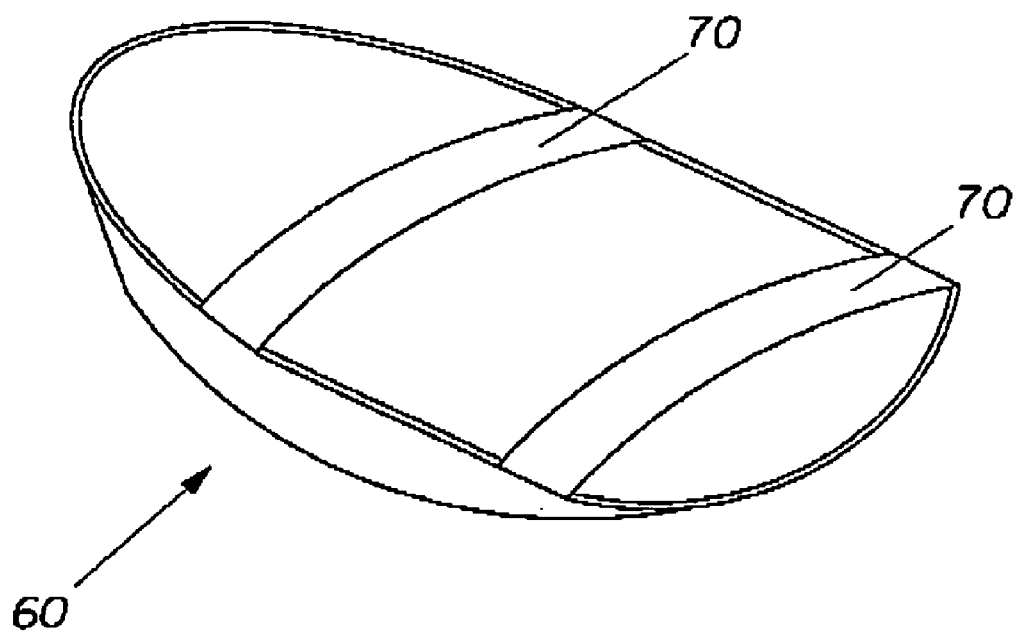
FIG. 8 is a perspective view of an open applicator.

Alternatively, it is also possible to add an elastic material to the mitt. This elastic material is preferably stretchable/deformable when it is subjected to mechanical constraints but it returns eventually to its original shape when the mechanical constraints cease. In one embodiment, an elastic material can be deformed of at least about 50% its original size without rupturing, preferably at least about 100%, more preferably at least about 200% and even more preferably at least about 300%. This material can be in the form of a string or a film This type of elastic material is well know in the art and non-limiting example of suitable elastic materials can be natural or synthetic rubber, spandex (segmented polyurethane fibers), Lycra®, and the like or elastic films/composites such as Kraton®. In one embodiment, a piece of elastic material 70 is stretched and attached to a portion of the mitt 10, preferably a portion located in the inner surface of the mitt, more preferably a portion located adjacent to the opening which can be for example the cuff. When this piece of elastic material returns to its original shape, the portion of the mitt to which this elastic material is affixed, retracts as well. A user can simply stretch this portion of the mitt in order to insert her hand. The elastic material allows the mitt to be removably secured to the user's hand. A piece of elastic material 70 can also be particularly beneficial for applicators 60 which comprise only one side such as the one represented in FIG. 8.

It is important to note that all the foregoing methods provide better control of the mitt to the user and that these methods can be combined. One skilled in the art will understand that the foregoing components and methods, which were described in relation with the wetting side of a mitt, can also be applied to the drying side of a mitt or to an applicator having a single wet or drying side.

In one embodiment, the wetting side 27 of a mitt can comprise at least a reservoir 227 which can be of any shape and size as long as it has the ability to contain the product and is controllably actionable by the user. The reservoir 227 will be later described in greater details.

As shown in FIGS. 3 and 4, the wetting side of a mitt also comprises at least a second layer of material 327 which can be a porous, preferably nonwoven, material through which the product, which in one embodiment can be contained in the reservoir 227, can be dispensed. The material used for the second layer can be either substantially non-absorbent or absorbent depending on the type of applications and the type of product that is applied to the surface. By substantially non-absorbent, it is meant a material which can generally absorb less than about 10% of its own weight such as for example, polyethylene, polypropylene, polyethylene terephthalate, Nylon, and biodegradable fibers such as Polylactic. This second layer of material 327 provides several benefits to the wetting side of a mitt. For example, when the product is a liquid contained in a reservoir 227 located between the first 127 and the second 327 layer, the second layer 327 provides a good distribution of the liquid and helps the liquid to wick away from the first layer of material and the reservoir. Depending on the kind of material used for this second layer, this second layer can also readily absorb at least a portion of the soils of the surface being cleaned. One example of material which is substantially non-absorbent is a polypropylene nonwoven fibrous material. This material can be particularly suitable when the product applied directly or indirectly to the surface is a fluid having a high viscosity such as a gel Another applicable substantially non-absorbent material can be an open or closed cell polyethylene foam, such as available from Sentinel Products Corp. of Hyannis, Mass. Suitable materials for use as the front panel or second layer of material 327 of the wetting side 27 also provide sufficient strength and texture characteristics so as to provide a scrubbing action upon the target surface and to maintain web integrity when exposed to a liquid. Additional, or alternative, fibers such as polyethylene terephthalate fibers can be utilized for additional strength and scrubbing capability.

Figure 9:
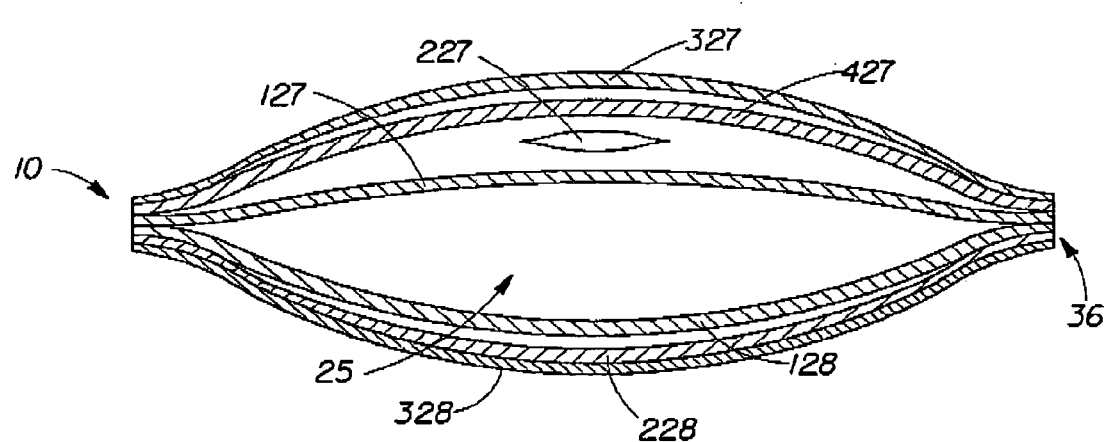
FIG. 9 is another cross-sectional view of a mitt of FIG. 1 taken along line 1—1.

In view of the fact that polypropylene nonwovens, and many other suitable materials for the second layer of material 327 of the wetting side 27, are highly porous and rapidly penetrated by liquids, the wetting side of the present invention can also include a tissue paper layer 427 between the reservoir 227 and the second layer of material 327, as represented in FIG. 9. A suitable material is a single ply of disposable kitchen paper towel such as BOUNTY®, a product of The Procter & Gamble Company. Such a material is capable of wicking the liquid of interest and distributing the liquid beyond the dimensions of the reservoir and supplying liquid to a larger surface area of the outer layer (front panel 27). This wicking layer may also be desirable to help control fluids of low viscosity as they are distributed to the front panel for dispensing.

In another embodiment of the invention, the second layer of material 327 is substantially entirely made of substantially non-absorbent synthetic fibers such has SMS, Celestra® from BBA of Simpsonville, S.C. The use of a entirely synthetic material can be particularly beneficial when the product applied to the surface to be cleaned, is chemically "aggressive" such as a hypochlorite or peroxyde bleach, a product with a high pH, or a product with a low pH. One skilled in the art will understand that when this type "aggressive" product is used, it can be preferred to avoid using a material comprising natural fibers which can deteriorate when in contact with such a product.

In a preferred embodiment of the invention, it can be beneficial to have the second layer of material 327 of the wetting side 27 made of a single layer of an absorbent material. This single layer of material can be made of a combination or "blend" of substantially non-absorbent and absorbent fibers. Among other benefits, this type of material can improve the fluid absorption and spreading which results in a better distribution of the fluid on the target surface. This single layer of material 327 can be particularly beneficial when the product is a liquid solution. In addition, the absorbent fibers of this material provide an enhanced soil absorption and helps to capture particles which are removed from the surface to be cleaned. The substantially non-absorbent fibers of this material, also facilitates the wiping of a hard surface, such as for example glass, in particular when this surface is wet. Among other benefits, the presence of substantially non-absorbent fibers in this single layer material 327 results in better cleaning, ease of use and better fluid release onto the surface. In this embodiment, the second layer of material is preferably non-woven and can be spunlace, air laid, carded, carded thermal bond, carded chemical bonded, carded through air bonded, wet laid, and any combinations thereof. The substantially non-absorbent fibers used for this material can be synthetic fibers selected from the group consisting of polyvinyl derivatives, polyolefins, polyamides or polyesters and any combinations thereof. The absorbent fibers used for this material can be synthetic and/or natural fibers and can be selected from the group consisting of cellulose, cotton, rayon, lyocell, linen, sisal or ramie and any combinations thereof. Any of the fibers can be treated with polymeric binder resin for binding and/or functional benefits including adsorption. For example, a 60/40 polypropylene/Rayon hydroentangled web typically about 60 gsm from Suominen or Pantex; a 100% polypropylene SMS from BBA, typically is a 43 gsm, a 70/30 Rayon/polyethylene terephthalate hydroentangled blend from BBA. In one embodiment, the second layer of material comprises from about 5% by weight to about 95% of substantially non-absorbent synthetic fibers and from about 5% to about 95% absorbent fibers.

Optional Reservoir

The wetting side of a mitt can optionally comprise a reservoir 227. In one embodiment, the reservoir 227 can be located between the first and second layers of the wetting side of the mitt. The reservoir 227 contains a product that may be dispensed and/or dispersed from the reservoir 227 to the outer surface of the wetting side, for delivery to a target surface. The fluid reservoir 227 may be of any suitable size, configuration, and composition for the intended product to be dispensed and dispersed. The product may be a liquid, a gel, a lotion, a cream, a powder, a solid, or any mixture thereof. A solid such as a wax, for example, may be heated to provide a flowable product that may be dispensed and/or dispersed from the reservoir 227. In another embodiment, the reservoir 227 may be a separate article that can be inserted into the mitt 10 by the user. For example, the reservoir 227 may be inserted inside of the wetting side of the mitt 10 through a slit or an opening or may be inserted into one or more pockets located between the front outer surface 31 and the front inner surface 32 that are designed to receive the reservoir 227. This allows the user to replace reservoirs 227 as needed and provides for reuse of the mitt 10 if it retains sufficient absorbency, wet strength, etc. In addition, the reservoir 227 can be part of a kit comprising at least one mitt 10 preferably having a wetting side. In one embodiment, the reservoir 227 can be sold separately from the mitt 10. The reservoir 227 can be a rupturable reservoir which will later be described, or it can also be a more simple tearable sachet or a sachet with a peelable label that the user opens by peeling off the label, thereby exposing the product dispensing apertures, slits, or combinations thereof. A user can "activate" or open the reservoir 227 and then apply the desired amount of product on the surface to be cleaned but preferably on the outer surface of the wetting side 27 of the mitt 10. The user can keep adding product on the wetting side if more product is necessary to finish cleaning the surface. One skilled in the art will understand that when a product is applied directly to the surface to be cleaned or to the outer surface of the wetting side of a mitt, an opening or slit is not required.

Figure 10:
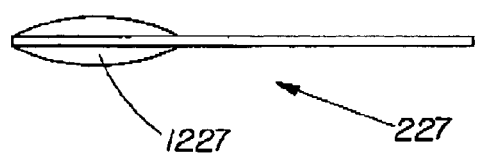
FIG. 10 is an elevational view of the rupturable reservoir of mitt of FIG. 1.
Figure 11:
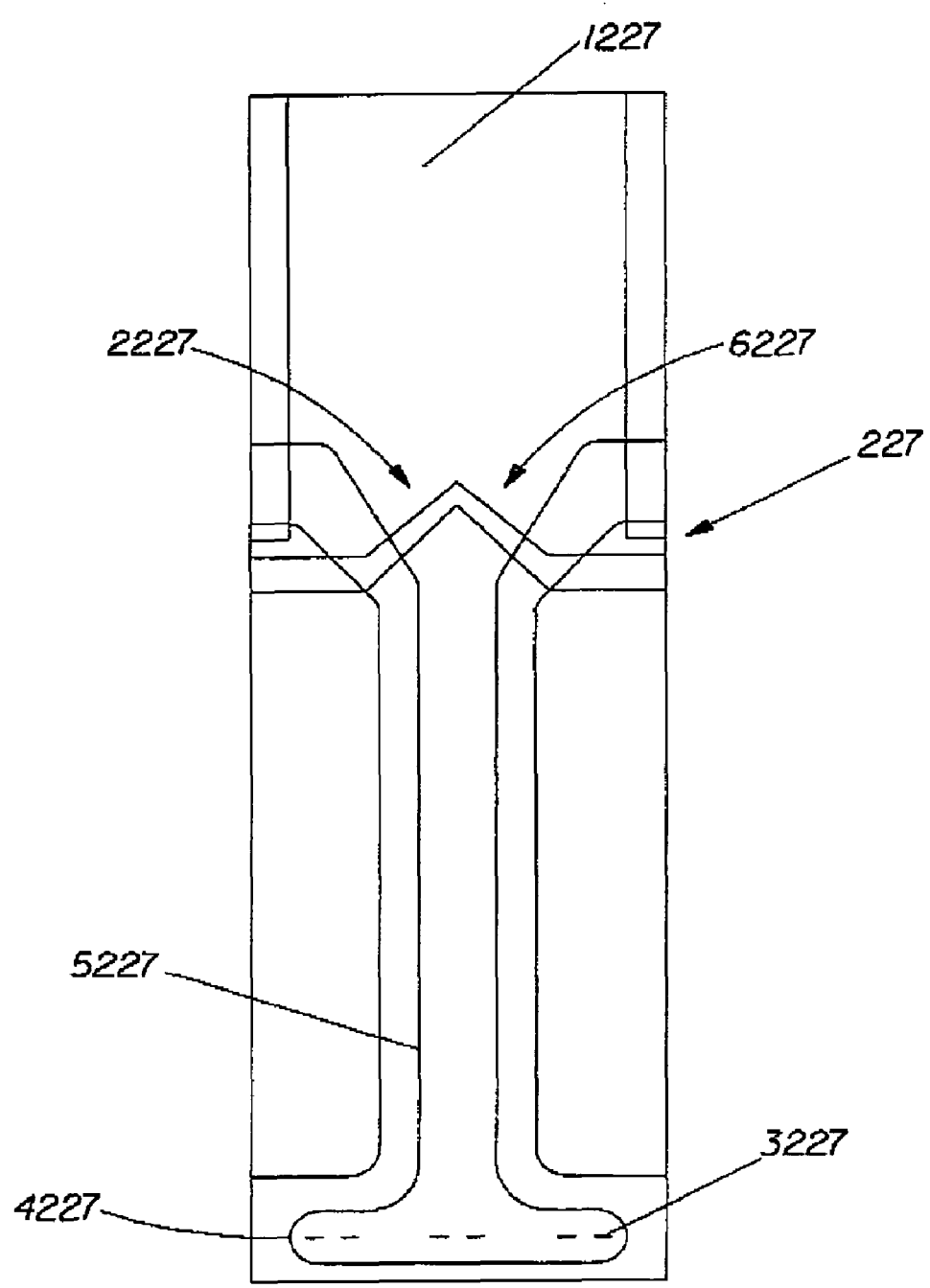
FIG. 11 is a plan view of the rupturable reservoir of FIG. 10.

When a reservoir 227 is located or inserted between the first and second layer of a wetting side, one aspect of the reservoir 227, which is believed to be important to the overall functionality of the mitt 10, is the ability of a sealed, fully-enclosed reservoir to rupture or otherwise dispense the product contained therein when "activated" by the user and yet resist premature dispensing during manufacture, packaging, and shipment. In alternate embodiments, the reservoir 227 may be located at least partially outside of the applicator 10. For example, chamber 1227 of reservoir 227 of FIG. 10 might extend outwardly from an applicator for improved visual and manual access, as desired. The ability of the reservoir to survive intact until the point of use preserves the quality and quantity of the liquid until the time of use. As will be understood, external accessibility to a reservoir might also facilitate the provision of crimping devices, folding of a reservoir or other protection of the reservoir against premature dispensing, as will be discussed further below. In one embodiment, the reservoir can be designed to burst or rupture to release the product contained within the reservoir at a comparatively low force when desired by the consumer. This may be accomplished by having a sealed pouch with permanent seals and also seals that are "frangible", i.e., rupturable. When the pouch is squeezed, the frangible seal will yield or fail first since it has a lower peel force to break the seal apart than the permanent seals. In one embodiment, the frangible seal will ideally rupture from about 0.5–10 lb, more preferably from about 1–6 lb and most preferably from about 1–3 lbs of force when applied by the consumer. Adding stress concentrators in the seal geometry that will localize forces at a particular location can optimize the location of rupture. These stress concentrators can be shaped like a V, a notch, a half circle or a variety of other shapes depending upon the desired burst level. These stress concentrators will help control the force required to burst the pouch as well as the location of where the seal will rupture. Such stress concentrators thereby focus or concentrate external pressure or mechanical forces imposed on the reservoir and its contents. For example, pressurizing a pouch having a V-notch 6227 seal such as shown in FIG. 11 will localize forces first at the apex of the V, causing that region to rupture first. Without intending to be bound by any theory, it is believed that a V-notch seal 6227 that is formed under the same conditions than a straight bar seal can require less force in order to rupture. The angle or "opening" of the V-notch seal 6227, the width and length of the seal, can individually or in combination be adjusted in order to create a seal with the desired burst force. Such an arrangement can help reduce potential variability in rupture or dispensing forces and the location where the rupture occurs. Additionally, other seal angles and geometries of the seal can also be used to tailor dispensing forces for particular applications.

Figure 12:
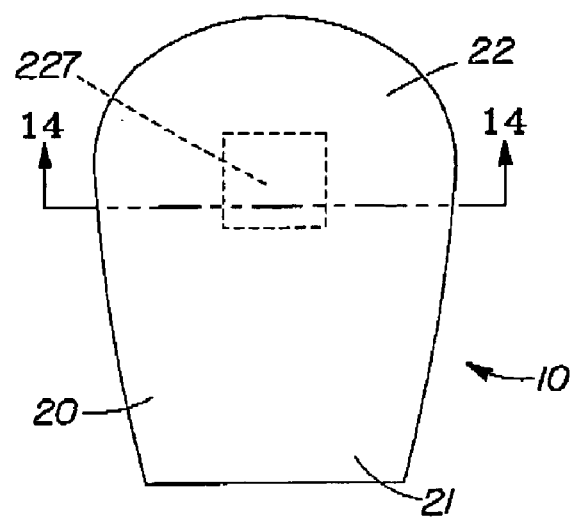
FIG. 12 is a plan view of a another embodiment of wetting side of a semi-enclosed applicator in accordance with the present invention, in the form of a mitt.

In the embodiment of FIG. 12, the reservoir 227 is positioned in the central portion 22 of the mitt 10. In this location, the reservoir 227 can be subjected to sufficient force to rupture the reservoir and dispense the liquid by making a fist with the user's hand, by applying force with the opposite hand, or by pressing the palm against the target surface. This location of the reservoir 227 in the applicator is convenient for applications where it is desired for the product to be dispensed all at once or while rubbing a surface. It may also be desired to have the reservoir located in a portion of the applicator that is spaced or remote from a location where forces are applied during cleaning or rubbing. In this manner, pressure applied to the mitt during cleaning or rubbing will not cause premature dispensing or dosing of the product in the reservoir 227. FIG. 1, for example, depicts an embodiment of a mitt 10 wherein the reservoir 227 is positioned close to the cuff region 21. In this location, the reservoir 227 is not located in a region of the mitt that would typically encounter forces in use (the application or pressure region), and the reservoir 227 would require activation by specifically applying force to the cuff region. Such an embodiment may be particularly advantageous where progressive dispensing of discrete quantities of the product is desired rather than an "all at once" dispensing upon application of an initial force.

The use of a reservoir 227 to contain a product allows the wetting side 27 to become wet only when wanted by the person using the applicator. In some cases a person would like to store a single applicator in a remote site such as a glove box in a car or in a separate drawer in a bathroom. The hermetically sealed reservoir(s) in the applicator preferably use sufficient barrier materials to allow these individual applicators to have multi-year shelf life even when stored as individual units. Separately, multiple reservoirs can be placed on the wetting side 27 of the applicator. In contrast, pre-moistened wet wipes that have been individually wrapped are traditionally placed in a foil pouch. This foil pouch material is expensive and more of it is needed to enclose the entire wipe to prevent moisture loss (with the individually enclosed reservoir, foil film is only needed to enclose the liquid or substance). This approach of putting the entire pre-moistened applicator (wipe) in a foil pouch also makes it difficult for the wipe to have a dry surface or from having surfaces with two different substances since cross-contamination is likely to occur.

FIG. 11 illustrates one suitable configuration for a rupturable reservoir 227 suitable for use with applicators 10 according to the present invention, such as the applicator of FIG. 1. In the embodiment of FIG. 11, the reservoir 227 includes a chamber 1227, a frangible seal 2227, and at least one dispensing aperture 3227. The embodiment of FIG. 11 may be made by peripherally joining two similarly-sized and shaped pieces of fluid-impervious material with substantially permanent seals, forming the dispensing apertures in one portion of at least one of the pieces of material, introducing the product through one of the apertures, and then forming a frangible seal of limited strength to separate the chamber 1227 from the apertures 3227. Other forming techniques, such as folding a single piece of material double upon itself and sealing, or rolling and sealing a piece of material to form a sleeve, may also be utilized. In a preferred embodiment the frangible seal is formed prior to the filling operation the reservoir. Forming the frangible seal prior to the filling operation can be beneficial to avoid product contamination of the frangible seal region on the film.

In another embodiment of a reservoir 227 that is functionally similar to that of FIG. 11, the reservoir 227 can include a plurality of chambers 1227 for containing liquid. Respective chambers 1227 may include product(s) of the same, similar, or diverse compositions, and may be designed to be ruptured sequentially or simultaneously depending on how pressure or squeezing is applied by the user. In another embodiment, a reservoir 227 can have a plurality of chambers 1227, but wherein the chambers are themselves separated from one another by the rupturable seal 2227. In such an embodiment, the chambers would typically be released concurrently, such as to mix the products from respective compartments at the time of dispensing.

The wetting side 27 of the present invention may have a burstable reservoir that has multiple chambers for mixing incompatible products. This would allow the ability to deliver superior cleaning performance as an example at an affordable cost. For instance, a chamber could have a bleach formula suitable for killing mildew, and germs and the other chamber could contain surfactants and cleaning solutions suitable for removing dirt and soap scum. The ideal formulas for these two different tasks are incompatible for a long period of time (like on a store shelf), but can be mixed right before use (like in the mitt) or can be dosed sequentially to deliver superior cleaning performance of nearly any type of bathroom stain. The same could be done for a variety of other uses like a disposable finger toothbrush that dispenses baking soda and peroxide on a "finger" mitt that allows these two products to be mixed to deliver superior teeth cleaning in a disposable package for away from home occurrences. The back side of the mitt could have a post-treatment for whitening the teeth.

More advanced product distribution functionality may be designed into the reservoir and/or to the applicator. The bursting pouch may also have an integral distribution head connected to the chamber 1227 via a channel 5227 (such as illustrated in FIG. 11) that allows the product to be dispensed and dosed to different portions of the mitt. This distribution head 4227 is ideally an extension of the pouch material that has been sealed in a way to form the channel(s) 5227 for the product to flow to another region. The distribution head 4227 may have holes or slits 3227 in the sides for the product to exit or may have several seals that force the product to change direction minimizing the velocity of the product exiting and thus eliminating or reducing uncontrolled spraying of the product out of the mitt. Other arrangements, such as the inclusion of baffling structure to divert or control the fluid might be desirable as well, such as where products of low viscosity are dispensed. A distribution head 4227 comprising a plurality of slits 3227 maximizes wicking and allows product to slowly weep out. The distribution head 4227 can be modified greatly to match desired product delivered.

One skilled in the art will understand that Fluid flow between the chamber 1227 and the channel 5227 is controlled by the frangible or rupturable seal 2227, which illustrates the use of a stress-concentration notch 6227. The channel 5227 may be of a material and configuration such that it is "self-sealing" and collapses shut to restrict, if not preclude, fluid flow except when the chamber is substantially pressurized. For example, a channel may be formed by making two substantially parallel seals along facing layers of a pouch, where the space between these seals becomes a channel for fluid to move from the reservoir to the distribution aperture(s). The channel will naturally lay flat (and thereby closed) due to the seals, but will become almost tubular when the reservoir 227 is pressurized and filled with fluid traveling through the channel. Upon release of the pressure, the channel will tend to naturally return to its flat state, causing a sealing effect to prevent further product delivery. The dimensions of the channel may be optimized based upon the viscosity of the product being dispensed from the reservoir 227. For example, a reservoir 227 designed for dispensing a powder or a relatively thick lotion or cream product will preferably have a wider channel than a reservoir designed for dispensing a relatively lower viscosity product such as a predominantly water or alcohol based product. In one embodiment, for example, the channel width is preferably in the range from about 0.1 inches to about 1 inch wide, more preferably about 0.25 to about 0.75 inches, to allow "resealing" of the channel while not requiring excessive force on the pouch to pressurize the channel. Resealing of the channel may provide for dosing or progressive fluid dispensing. The outlet ducts and/or the apertures may be used as desired, with one or the other being employed or both in combination. In a preferred embodiment, the flow can be regulated by changing the size of the dispensing apertures or slits. In FIG. 11, the channel 5227 provides a path to transport the fluid from the chamber 1227 to the distribution head 4227. The number of dispensing slits 3227, their size and location can allow to control and to obtain the desired flow rate from the chamber 1227. In one embodiment, a plurality of slits can be located in the distribution head. These slits are positioned in the distribution head such that the fluid is released on a greater surface of the wetting side of the applicator. In a preferred embodiment, three slits are positioned in the distribution head. Other approaches to provide dosing capability (i.e., multiple discrete dispensing cycles) include providing multiple reservoirs on either or both sides of the applicator.

Figure 13:
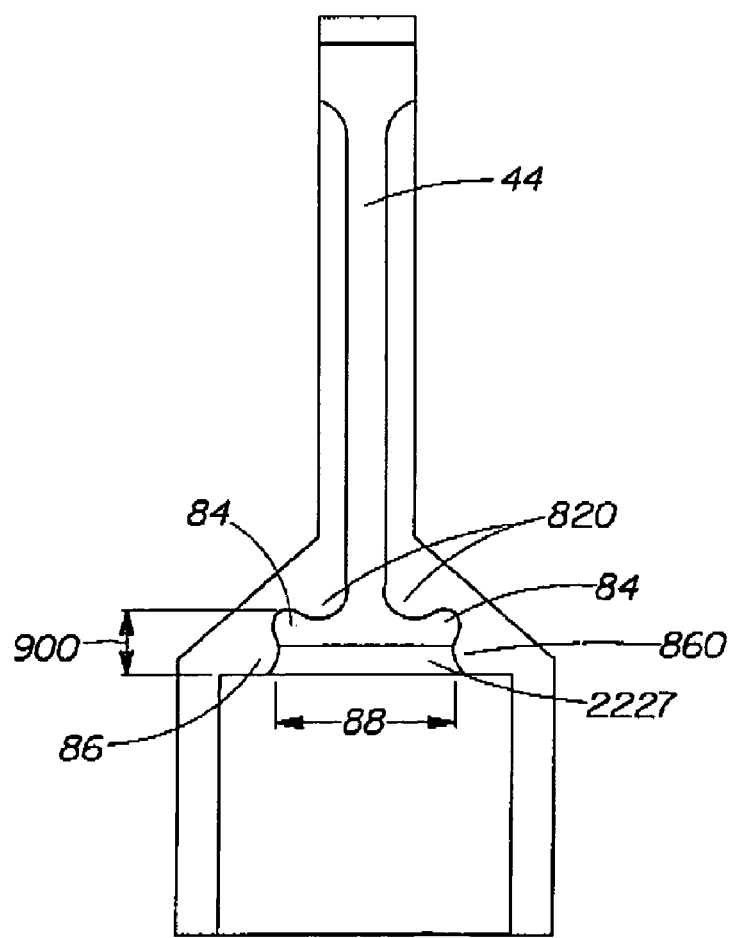
FIG. 13 is a plan view of another suitable rupturable reservoir in accordance with the present invention.

Additional functionality may be added by providing dosing. FIG. 13, for example, shows one such embodiment with additional features for controlling dosing. Areas 820 of the lock up seal aid in the prevention of over-dosing by inhibiting fluid flow through the dosing channel once activated. Thus, the user feels an increase in resistance when squeezing or pressing the pouch. Areas 840 are preferably not sealed and extend beyond the end of the dosing channel. Once the cell is pressurized, these areas 840 fill and provide a more rigid three-dimensional structure to the cell and prevent the channel from folding and clamping shut. Areas 860 of lock up seal can be added to provide a "target zone" for the frangible seal. Thus, burst force consistency is improved by limiting the width 880 of the frangible seal 2227 and manufacturing is made easier by having a larger zone 900 where the frangible seal can be located. Area 860 also aids in forming a natural fold line for protecting the frangible seal.

Dosing may alternatively be accomplished without the use of a dosing reservoir or distibution channel. For example, a rupturable reservoir such as shown in FIG. 11 or 13 may be combined with a flow restriction layer. The flow restriction layer may be a separate layer in the mitt 10 such as the front panel surface 27, the layer 327, or be an additional layer that is between layer 327 and the reservoir 227. Nonwovens, apetured films, thermoformed films, and other materials, for example, can be created to have a target porosity and thus fluid flow rate. Controlling the mean pore size of openings and the number of openings in the flow restriction layer can determine how fast a fluid or product will be dispensed through the front or back panel. The fluid flow rate can be controlled by incorporating the desired porosity in the front or back panel materials or can be accomplished by having a separate layer or layers between the reservoir 227 and the application surface of the mitt 10. An example of a flow restriction layer is a 100 mesh hydroapetured film made from low density polyethylene. The apertures in this structure are approximately 100 micron in diameter and may be suitable for controlling the fluid rate of creams and lotions, for example. The number and size of the holes can be adjusted depending upon the viscosity of the fluid being dispensed and the desired application rate.

A reservoir 227 having a frangible seal connected to a distribution channel 5227 such as shown in FIG. 11, for example, can provide fluid communication with one or more distribution apertures located in a region or application surface of the mitt removed from the location of the reservoir 227 itself. As shown in FIG. 1, for example, a reservoir 227 can be located near a cuff region of the mitt such that the reservoir 227 and the frangible seal 2227 are located below the palm of the wearer's hand and the distribution channel 5227 provides fluid communication to a portion of the mitt corresponding to the position of a user's fingers in use. In one embodiment, the distance from the tip of the closed side of the mitt 10 where the fingers of the wearer's hand are located to the frangible seal 2227 can be in the range from about 5 inches to about 9 inches thus allowing the frangible seal to remain clear of the pressure applied by the palm of the wearer's hand of about the 97.5 percentile of women (7.5 inches) and of the 97.5 percentile of men (8.2 inches). See, e.g., Dreyfuss, Henry, *The Measure of Man*, New York; Whitney Library of Design (1969). This location, for example, can space the reservoir away from the region of the mitt that would typically encounter application and scrubbing forces in use, and may allow for sequential dosing of the product in the reservoir by requiring activation by specifically applying force to the cuff region for selectively dispensing the fluid. In this embodiment, the fluid would travel through the channel to the distribution head where the fluid is released on the desired location of the mitt, such as near the fingers in the preferred embodiment. The channel length, e.g., the distance from frangible seal 2227 to the distribution head 4227 shown in FIG. 11, is preferably in the range from about 0.5 inches to about 8.5 inches long, more preferably in the range from about 3.5 inches to about 5 inches long.

The reservoir 227 preferably uses a laminate film that contains either metallized polyethylene terephthalate, aluminum foil, $SiO_2$ or some other high barrier material that will provide an adequate moisture and/or oxygen barrier to allow the product to have a reasonable shelf life. In one embodiment, for example, the reservoir may have a shelf life in the range from about 2 years to about 3 years. Smaller reservoirs with small amounts of a product require even a higher barrier since the surface area to volume of fluid is significantly higher resulting in higher levels of moisture loss due to transport and diffusion.

The reservoirs can be made rupturable or "frangible" by a number of different techniques. One preferred technique is to make a pouch on a vertical or horizontal form/fill/seal machine that has the ability to make different seals on the pouch at different temperatures, pressures or seal times. This allows one side of a pouch to have different sealing conditions that in turn can allow one side to have a weaker seal strength. A suitable sealant material for this type of "frangible" seal would be Surlyn® made by Dupont or a blend of Polybutylene with Ethylene Vinyl Acetate or ultra low density ethylene copolymers, polyolefin plastomers, and/or Polyethylene. Sealant layers made with either of these resins or blends will result in a sealant layer that will have significantly different seal strengths depending upon the seal temperature. The blend provides a "contaminant" to the base polymer material that allows the resulting seal to be selectively frangible under certain sealing conditions. For example, at 200 degree F. the sealant layer will deliver a seal force of 200–400 grams/linear inch of seal width and at 300 degree F. the seal force will deliver a seal force closer to 3000 grams/linear inch of seal width. This variation in seal strength allows a pouch to be "welded" shut in one portion and easily burstable in a second portion just by adjusting the seal temperature, the seal time and/or the seal pressure used when making the pouch seals (e.g., the pouch may be welded along all or a portion of one, two, three or more sides and easily burstable along a portion of one, two, three or more sides). A preferable film structure for this type of frangible reservoir would be Surlyn sealant/tie layer/metallized polyethylene terephthalate. Other techniques for making the consumer activated rupturable reservoirs include delaminating seals, weak regions in the film structure such as created by embossing, laser scoring, mechanical scoring or other known methods of weakening a film structure, and small thermoformed cells with thin regions that rupture when squeezed (similar to bubble wrap). Alternatively, a reservoir 227 may have other opening means such as tear-off strips, pull tabs, release liners and the like.

Figure 14:
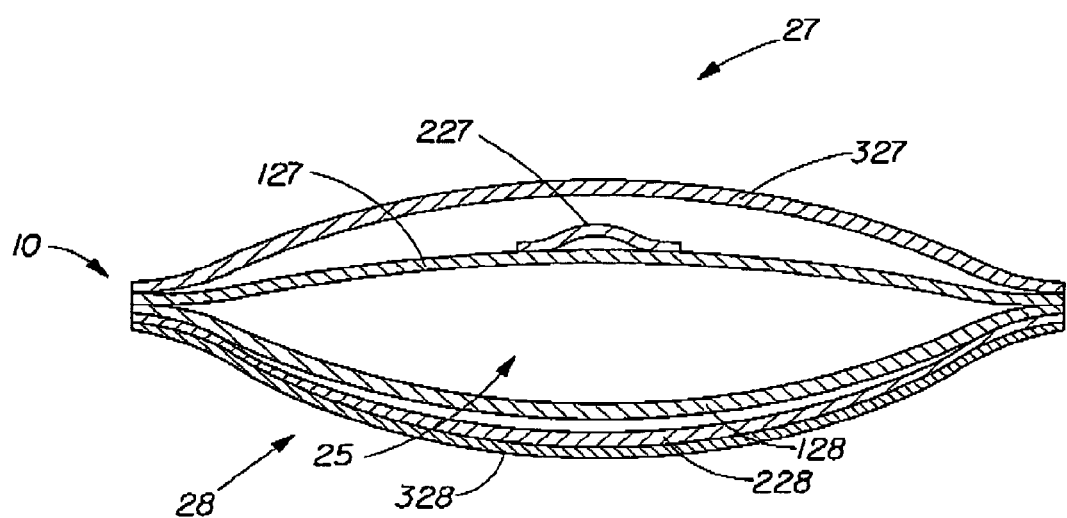
FIG. 14 is another cross-sectional view of a mitt in accordance with the present invention.

One skilled in the art will understand that the reservoir 227 can be made as a separate element and be placed between the first 127 and second layer 327 of the wetting side 27. In another embodiment of the invention, a reservoir 227 can be integrated onto the first layer 127 of the wetting side of the mitt. A cross-sectional view of this embodiment is represented in FIG. 14. When the product is a liquid, the first layer of the wetting side is preferably made of a fluid impervious material such as the ones previously described. The reservoir 227 can be integrated to the first layer of the wetting side by applying another layer of fluid impervious material on the top of the first layer and then form the required permanent and frangible seals as previously described.

In one embodiment, the reservoir 227 is made as a separate element and can be adhesively attached to the first layer of material and/or the second layer of material of the wetting side.

Drying Side

In accordance with one aspect of the present invention, the mitt 10 can comprise a drying side 28. By drying side, it is meant a panel of the mitt which can be used to remove particles such as dust from a surface and/or to dry and/or buff a surface after wet cleaning. After the product has been dispensed and dispersed onto the target surface, for example, it is sometimes desirable to absorb and remove excess product, contaminates and/or particles from the target surface while minimizing filming, streaking and/or residuals.

In one embodiment, for which a cross-sectional view is represented in FIG. 3, a drying side comprises at least a first layer of material 128, an absorbent core 228 for absorbing a product and a second layer of material 328. Once a mitt 10 is formed and the user inserts her hand in the mitt, the first layer 128 of material will typically be in contact with the user's hand. The first layer 128 can be made of a heat sealable material, i.e. a material which is thermally bondable. As previously described, a heat sealable/thermally bondable material is particularly beneficial since it allows two or more layers of material to be thermally bonded without requiring an adhesive to be used. For example, the first layer 128 of a drying side 28 can be thermally bonded to the first layer 127 of a wetting side 27 to for a "chassis" along their periphery to form the seam 36. Additional layer of material can also be added on the top of the first layer 128 of the drying side 28 and thermally bonded to the "chassis." In one embodiment, additional layers can be thermally bonded and/or adhesively attached to the chassis. The first layer 128 of the drying side can be made of a fluid pervious or fluid impervious material depending on the kind of application. In one embodiment, a drying side can comprise at least three layers being an inner layer, a middle layer, which can be an Absorbent Core, and an outer layer. In this embodiment, the inner layer and the outer layer can be thermally bonded such that the middle layer is trapped in between. This embodiment might be particularly beneficial when a middle layer is made from a material which is not thermally bondable or a material which is thermally bondable but which would require a longer time to be thermally bonded due to thickness or high melting point.

In one embodiment, the first layer 128 is fluid impervious but it allows air to circulate. Such a material can be particularly beneficial since it allows perspiration from the hand of the user to be evacuated while preventing a liquid such as a cleaning solution to get in contact with the user's hand. Non-limiting example of suitable material can be "breathable" material such as Aptra® Classics from RKW Films Corp, Wasserburg, Germany.

The drying side 28 of a mitt 10 also comprises an inner Absorbent Core 228 for absorbing the product and retaining the soil, dirt and particle of the wetted surface. This Absorbent Core can be made of any absorbent material known in the art. Non-limiting examples of absorbent material suitable for the Absorbent Core 228 include man-made fibers derived from cellulose (e.g., rayon, cellulose acetate, cellulose triacetate, lyocell) and natural cellulose fibers (e.g., from trees, cotton, flax). Other examples of absorbent materials include particles and fibers made from superabsorbent polymers (e.g., crosslinked copolymers of acrylic acid) Accordingly, the Absorbent Core 228 of the drying side 28 can be made from a material that is substantially absorbent for the product of interest. For example, the Absorbent Core 228 can be made of absorbent fibers that swell when exposed to the product of interest (e.g., liquids such as water, oils, etc.). Additionally, or in the alternative, the Absorbent Core 228 can be made of nonwovens, apertured films, absorbent or fibrous absorbent materials, super absorbent polymer fibers or powders, or laminates and/or combinations thereof. Absorbent nonwovens may be made by methods such as spunlace, spunbound, meltblown, carded, carded thermal bonded, carded chemical bonded, needle punched, air-laid, wet-laid and combinations thereof. In one embodiment, for example, the Absorbent Core 228 preferably has sufficient capacity to absorb four or more times its own weight of a liquid product. For aqueous liquids, four plies of disposable kitchen paper towel such as BOUNTY®, a product of The Procter & Gamble Company, has been found suitable for use. This paper towel material typically has the capacity to absorb between about eight and about nine times its own weight in water and will naturally retain the liquid more so than a thermoplastic non-woven material, for example. The fibers in the absorbent paper towel material will absorb the liquid and will swell to some extent as the liquid is absorbed. Further, absorbent foams such as those described in U.S. Pat. No. 5,571,849 issued to DesMarais may also be suitable for use as the Absorbent Core 228. In one embodiment where a mitt comprises a wetting side 27 having a reservoir 227 and a drying side 28 with an Absorbent Core 228, this Absorbent Core 228 preferably has sufficient absorbent capacity to absorb the quantity of liquid dispensed from the reservoir without oversaturating or substantially losing its web integrity. For example, the absorbent layer preferably has in the range of about two to about eight times, and more preferably in the range of about three to about five times, the absorbent capacity of the volume of the liquid within the reservoir 227. In one embodiment, if the reservoir 227 contained about 8 cc's of liquid product and the back panel 26 comprised a BOUNTY® paper towel that holds about eight times its weight in water, then to have two times the absorbent capacity a total of about 2 grams of the paper towel would be desired. Similarly, about 8 grams of the paper towel material would be required if an absorbent capacity of about eight times the capacity of the reservoir 227 cc's. The extra absorbency will further aid in achieving a streak-free shine because the Absorbent Core 26 will be able to remove nearly all of the liquid on the target surface, therefore reducing the formation of film or streaks of cleaning solution on the target surface. Further, as known in the art, certain materials may have a relatively higher capillary action which improves the absorption and transport of a liquid towards an unsaturated portion of the absorbent material used for the Absorbent Core and as a result less absorbent material may be needed. In one embodiment, for example, a structure such as those described in U.S. Pat. No. 5,571,849 issued to Desmarais, can be used for the Absorbent Core 228. In one embodiment, the Absorbent Core 228 can have an absorbent capacity substantially equal to the volume of liquid contained in the reservoir and may still offer an acceptable soil and liquid removal from the target surface. Without intending to be bound by any theory, it is believed that due to evaporation, absorption into the target surface, and other effects, the Absorbent Core often does not need to absorb the entire quantity of delivered fluid.

One possible use of a mitt comprising a drying side 28, can be for a user to contact the surface with the outer surface of the drying side 28 in order to remove/absorb the excess of product, soil, dirt and/or particles. In order to wipe a surface with the mitt 10, a user will have to overcome a certain amount of resistance due to the frictions between the outer surface of the drying side and the surface to be dried. All the previously described components and methods, which provide the user with better control of the mitt in relation with the wetting side 27 of the mitt, can also be applied to the drying side 28 of the mitt. In one embodiment, the drying side 28 comprises a second layer 328 of material which will be in direct contact with the surface which needs to be dried. It has been found that depending on the type of material used to make this second layer, it is possible to control the amount of force required to move the drying side of the mitt against the target surface and as a result improve the glide of the mitt on the target surface. One way to achieve this result is to make this second layer 328 from a material or a blend of materials which, when wetted, generates less drag compared to a material substantially made of absorbent fibers such as, for example, paper towel. This second layer of material also allows the product to "reach" the Absorbent Core 228 and is preferably a fluid pervious material. This material can be a blend of absorbent material and substantially non-absorbent material. In one embodiment, the substantially-non-absorbent fibers are synthetic fibers. The second layer 328 of material can be a blend of material comprising from about 20% to about 90% of an absorbent material and from about 10% to about 80% of a substantially non-absorbent material. Non-limiting examples of suitable material for this second layer can be: a 70/30 Rayon/polyethylene terephthalate spunlace of 50 gsm from BBA of Simpsonville, S.C., an 80/20 Rayon/polyethylene terephthalate pattern 16C apertured web from PGI or an 70/30 Rayon/polyethylene terephthalate 22×24 aperture pattern from PGI.

In one embodiment, the Absorbent Core 228 is preferably substantially in direct contact with the second layer 328 (outer layer) of material. While being capable of maintaining an acceptable absorbent capacity, it might be beneficial to size the Absorbent Core such that the surface of the Absorbent Core 228 is smaller than the surface of the second layer 328 of material which defines the outer portion/surface of the drying side 28 of the applicator 10. Among other benefits including material cost savings, it is believed that it is easier for a consumer to use and manipulate the applicator as well as being able to clean hard to reach areas when the surface of the absorbent core is smaller than the surface of the outer layer of the drying side. In one embodiment, the surface of the Absorbent Core which is in contact with the second layer of the drying side is equal to at least about 10% of the surface of the drying side of the applicator, preferably at least 20%, more preferably at least about 33%, even more preferably at least about 50%. In another embodiment, the surface of the Absorbent Core 228 which is in contact with the second layer 328 of the drying side 28 is equal to less than about 90% of the surface of the drying side of the applicator, preferably less than 80%, more preferably less than about 66%, even more preferably less than about 50%.

In yet another embodiment of the invention, the drying side 28 of a mitt comprises a first layer 128 of material and at least a second layer of material 228. In this embodiment of the invention, the first layer can be made of a thermally bondable material which can be used to form a chassis with another layer of a thermally bondable material as previously described. The second layer of material can be made of an absorbent material such as the ones previously described in relation with the Absorbent Core 228.

Types of Mitts/Applicators

In one embodiment of the invention, a semi-enclosed applicator can be a mitt having two wetting sides such as the ones previously described, each wetting side having at least one reservoir containing a product. This mitt can be made by forming a "chassis" with the two layers of heat-sealable material of each wetting sides. The reservoir and the outer layers covering the reservoir can be thermally bonded and/or adhesively attached to the "chassis". In this embodiment, the product contained in each wetting side can be identical or can have different properties depending on the kind of application.

In another embodiment, a mitt can have a wetting side having a reservoir and a drying side. This mitt can also be made by forming a chassis.

In another embodiment, a mitt can have a single wetting side having a first layer of heat sealable material thermally bonded to a second layer of heat sealable material which can be a pervious or impervious film. This embodiment might be particularly suitable for small cleaning jobs, in particular those which do not require the target surface to be dried. The other layer of material is beneficial to form a mitt and prevents the soil/dirt, the liquid or any other product to get in contact with the consumer's hand during use of the mitt.

In another embodiment, an opened "cleaning" applicator can comprise a wetting side, optionally a reservoir such as the one previously described and means for removably securing the cleaning applicator on the user's hand. Non-limiting examples of means for removably securing this applicator can be one or more strips of elastic material attached on each side of the applicator, strips of hook and loop fasteners, pressure sensitive adhesive having tacky properties at ambient temperature, slit(s) in the first layer of material of the wetting side of this applicator such that the user can insert at least a portion of her hand in this slit.

In another embodiment of the invention, a mitt can have two drying sides such as the ones previously described, each wetting side having an Absorbent Core. This mitt can be made by forming a "chassis" with the two layers of heat-sealable material of each drying sides.

In another embodiment, a mitt can have a single drying side secured to a layer of material which can be a thermally bondable pervious or impervious film. This embodiment might be particularly suitable for small jobs and when the user does not want her hands to get in contact with the target surface, liquids, soil/dirt or any other products during the use of the mitt.

In another embodiment, an opened absorbing/drying applicator 60 can comprise a drying side 28, such as the one previously described and means for removably securing the cleaning applicator on the user's hand. Non-limiting examples of means for removably securing this applicator can be a strip of elastic material 70 attached on each side of the applicator to for a deformable cuff, strips of hook and loop fasteners, pressure sensitive adhesive having tacky properties at ambient temperature, slit(s) in the first layer of material of the wetting side of this applicator such that the user can insert at least a portion of her hand in this slit. This embodiment is represent in FIG. 8

Manufacturing Process

Figure 15:
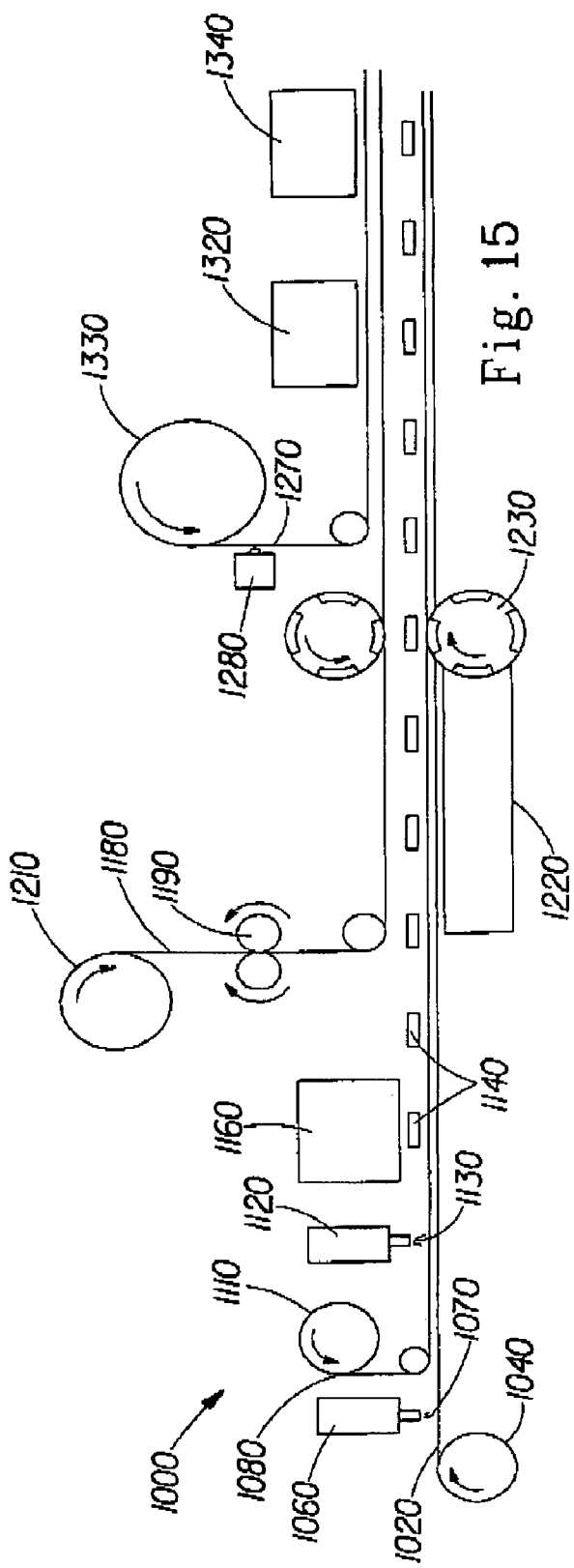
FIG. 15 is a schematic illustration of an applicator manufacturing process in accordance with the present invention.
Figure 16:
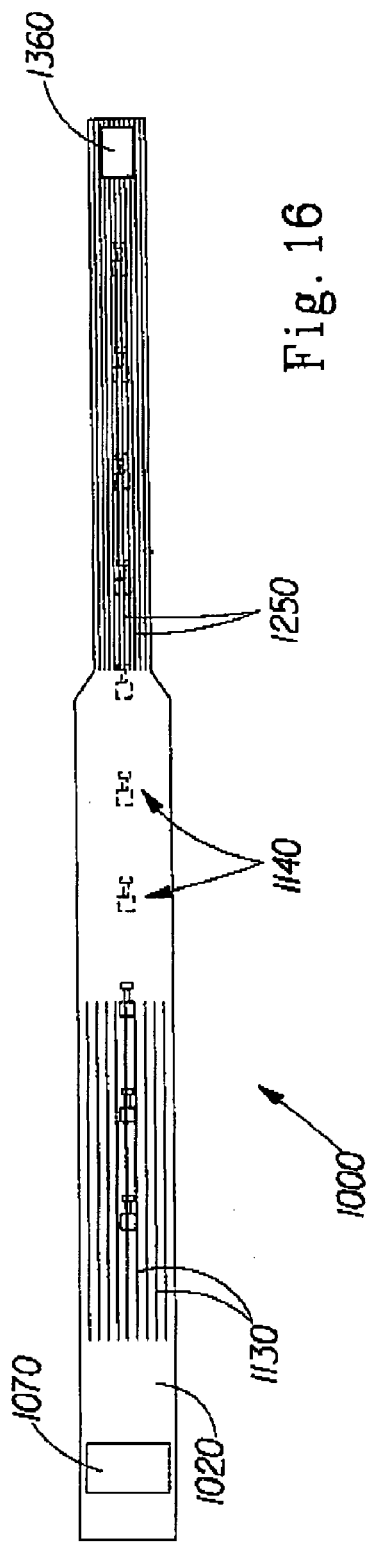
FIG. 16 is a plan view of the process of FIG. 15.

A manufacturing process suitable for manufacturing applicators in accordance with the present invention is schematically illustrated in FIGS. 15 and 16.

As shown in FIG. 15, the process 1000 begins with the feeding of a first web 1020 from a supply roll 1040. The first web 1020 corresponds to the front panel 240 of FIG. 1. A glue applicator 1060 applies a thin layer of adhesive 1070 to the upper surface of the first web 1020 in a suitable pattern for substantially uniform coverage, such as a spiral pattern as shown more clearly in FIG. 16. The adhesive is used to establish a bond between the first web 1020 and the second web 1080, which is fed from a supply roll 1100, to form a composite web. The second web 1080 corresponds to the Absorbent Core 228 shown in FIG. 2.

Once the first and second webs are secured to form a composite web, at least one reservoir 1140 (corresponding to the reservoir 227 of FIG. 1) is placed in an appropriate location in relation to the web dimensions so as to be located within the dimensions of the finished applicator. Any suitable apparatus 1160, such as a "pick and place" apparatus, may be utilized to place the reservoirs 1140 upon the traveling composite web. Beads of adhesive 1130 from an adhesive applicator 1120 may be utilized to secure the reservoirs 1140 in place.

Next, the third web 1180 corresponding to the barrier layer 127 of FIG. 3 is applied, first being fed from a supply roll 1200 through a pair of opposing rolls 1190 which perform the "elasticizing" operation to selectively strain the web to impart elastic-like properties, as described above. The web 118 is then applied to the composite web over the reservoirs 1140, and is held in a tensioned condition via the use of any suitable apparatus 1220, such as a "vacuum conveyor". The web is preferably stretched by at least 30%, and preferably at least 50%, to obtain the desired level of rugosities. The composite web then passes through a sealing/bonding apparatus 1240, such as a pair of compression rolls (with cavities as necessary to avoid prematurely rupturing the reservoir 1140), which bonds the composite web together with the barrier layer in the stretched condition. As best seen in FIG. 16, the cross-direction tension on the composite web is then released and the contraction of the third web causes the first and second webs to corrugate or pleat to form the plurality of rugosities 1250, corresponding to the rugosities 3217 of FIG. 7.

Finally, the fourth web 1260 corresponding to the back panel 28 of FIG. 2 is unwound from supply roll 1300, optionally coated with a friction-enhancing substance from applicator 1280, and then applied to the composite web. As mentioned earlier, friction-enhancing elements can be added in various forms such as panels, strips and beads, in addition to coatings. Consequently, such elements could alternatively be added to one or more of the webs joined to define the internal cavity as described, such as by adhesive, spray coating, heat sealing or other lamination techniques as known in the industry. A suitable apparatus 1320 such as a continuous rotary heat sealing apparatus then joins the fourth web to the remainder of the composite web by forming a peripheral heat seal around the edge of what will become the finished applicator, such as a mitt, in the desired outline shape. A rotary die cutting apparatus 1340 then severs the finished applicator from the excess material of the rest of the web to form finished applicator or mitt 1360. Finished applicators may then be folded, if desired, via the use of folding boards or other suitable apparatus (not shown) and packaged as desired.

Processing conditions for the above process may be determined in accordance with procedures known in the art for establishing suitable operating conditions such as seal temperatures, nip pressures, line speeds, and the like.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

For example, a mitt that fits on at least a part of one or more fingers only may be preferable for getting into tight spots or for better dosing control and dispensing accuracy. Applications for these finger or digit mitts would include applicators for facial creams, anti-wrinkling creams, cosmetics, liquid foundation, toothpaste, sunscreen, and others. The finger mitt would have a similar construction as the hand mitts but would be sized to only fit part of one or more fingers.

Another example would be a facial lotion that could be applied close to the eyes with a finger applicator. This applicator would allow the consumer to very precisely control where the product was applied without fear of getting in the eye. A suitable soft substrate such as an open or closed cell polyethylene foam could be used as the applicator substrate or front panel 27 to provide a very soft and smooth application surface for applying the product. Bristles (e.g. 190) or abrasive coatings can be applied to either substrate to provide additional scrubbing or cleaning capability. One way to apply bristle like fibers to the substrate would be to use a hot melt screen printing process as known in the art, where the adhesive pattern printed is elongated in a direction generally perpendicular to the substrate cleaning bristles extending upwardly from the substrate.

These smaller mitts would preferably be formed of a substrate such as front panel 27 for applying the product, a rupturable reservoir 227, a barrier layer 127 to keep product from contacting the skin, and a second substrate to create the internal cavity for the finger. The second substrate can also be designed to absorb liquid in the same way as the larger mitts for the hands. Of course, mitts could also be designed to go onto the foot, toes, or a reusable molded applicator part (not shown) meant to be used as an application device. The barrier layer and/or the substrates can also be made at least partially extensible, and can include a friction enhancing element as described herein to better fit and stay on the finger. Other alternatives and modifications will be apparent to those skilled in the art without departing from the scope of the present invention.

Figure 17:
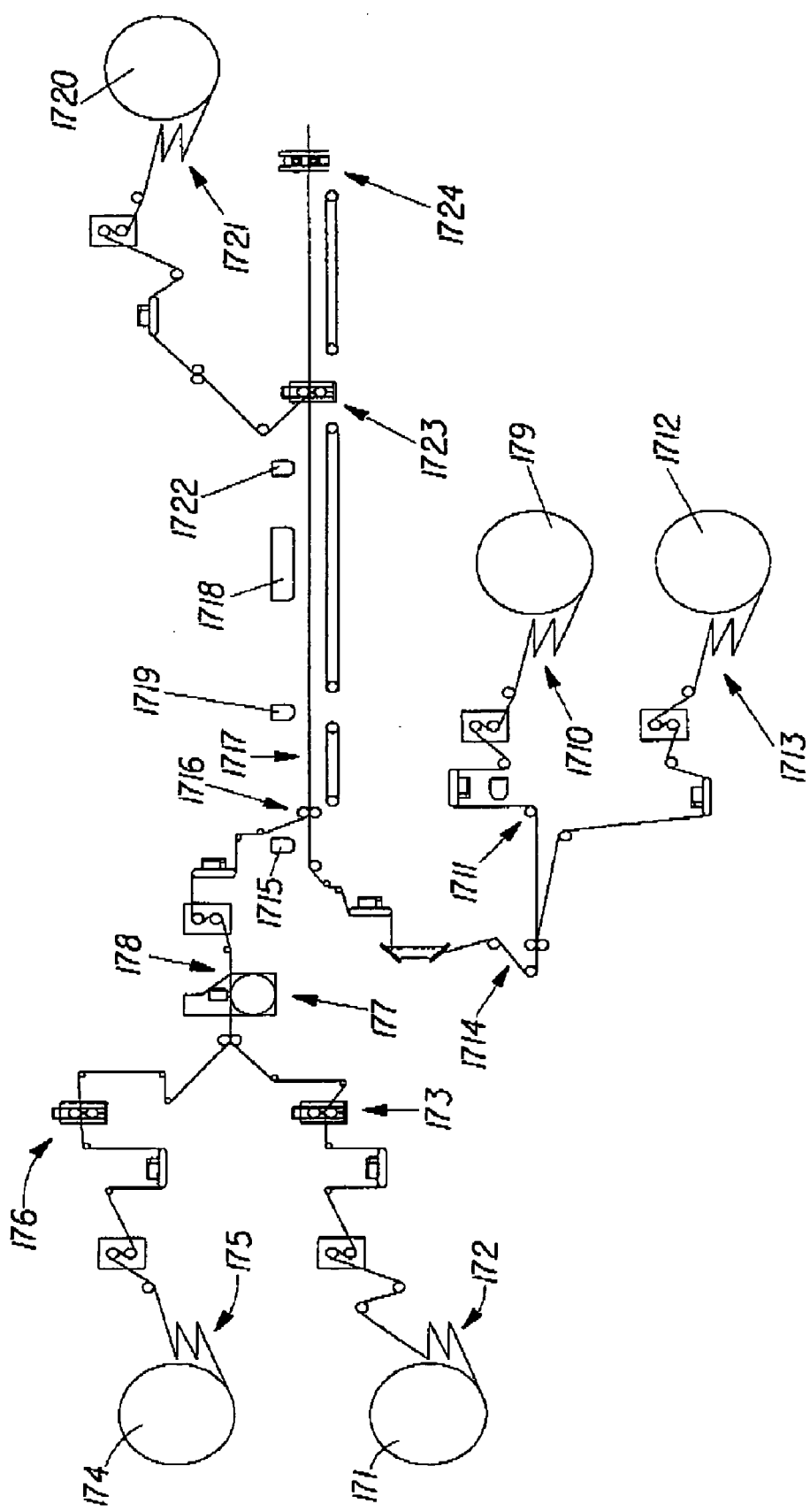
FIG. 17 is a schematic illustration of another applicator manufacturing process in accordance with the present invention

Another manufacturing process suitable for manufacturing the previously described applicators in accordance with the present invention is schematically illustrated in FIG. 17.

As shown in FIG. 17, the process begins with the feeding of a first web 172 from a supply roll 171. The first web corresponds to the drying side constituent of the poly to poly chassis. The drying side web can be fed through a set of opposing rolls 173 for the purpose of imparting an embossed pattern on the web before being combined with the wetting side constituent 175 at the web combining operation 174. The wetting side constituent 175 can also be fed through a set of opposing rolls 176 for the purpose of imparting an embossed pattern on the web. The combining operation 177 serves to impart sufficient pressure and/or heat to cause a bond between the two webs, thereby creating a mitt chassis. The web bonding operation can be accomplished using ultrasonic bonding, heated crimp, high pressure bonding, or the like.

Once the drying side and wetting side webs are bonded or secured to form a chassis 178, the drying side absorbent panel 1714 is adhesively attached. The drying side absorbent panel 1714 is formed from one layer or a multiple layer of webs. As shown in FIG. 17, a web 1710 is fed from supply roll 179. An adhesive 1711 is applied to the web for the purpose of bonding web 1710 to an additional web 1713 fed from supply roll 1712. The combined web formed by web 1710 and web 1713 forms the drying side panel material web 1714. An adhesive 1715 is then applied from an adhesive applicator to the drying side panel material web 1714 for the purpose of bonding web 1714 to the drying side of the heretofore formed chassis 178. A pressure nip 176 serves to apply pressure between the chassis 178, the adhesive 1715 and the drying side absorbent panel 1714, thereby causing a bond creating a new chassis 1717.

Once the chassis and the drying side absorbent material are secured to form a composite web, at least one reservoir 1730 (corresponding to the reservoir 227 of FIG. 1) is placed in an appropriate location in relation to the web dimensions so as to be located within the dimensions of the finished applicator. Any suitable apparatus 1718, such as a "pick and place" apparatus, may be utilized to place the reservoirs 1730 upon the traveling composite web. Beads of adhesive from an adhesive applicator 1719 may be utilized to secure the reservoirs 1730 in place.

Next, the wetting side applicator panel web 21 is delivered to the manufacturing process from supply roll 20. The wetting side applicator panel web 21 can be supplied to the process with a pre-embossed pattern in the web. Adhesive 22 is applied to the wetting side of the chassis by an adhesive applicator for the purpose of securing the wetting side applicator panel 21 to the wetting side of the chassis 17. A pressure nip 23 serves to apply pressure between the wetting side applicator panel web 21 and the adhesively coated wetting side chassis 17, thereby causing a bond between the two items. A rotary knife 24 is then utilized to separate the assembled mitt from the combined web to form a mitt.

What is claimed is:

1. A disposable semi-enclosed applicator for distributing a substance onto a target surface, said applicator comprising:
   (a) a first panel, said first panel comprising a first inner layer, a first outer layer and a reservoir positioned between said first inner layer and said first outer layer, wherein said reservoir is dispensible through said first outer layer; and
   (b) a second panel, said second panel comprising a second inner layer, a second outer layer and an absorbent core positioned between said second inner layer and said second outer layer;
   wherein said first panel and said second panel are attached to form a cavity in between and wherein said first inner layer is made of a thermally bondable material.

2. The disposable applicator of claim 1 wherein said second inner layer is made of a thermally bondable material.

3. The disposable applicator of claim 2 wherein said first inner layer and said second inner layer are thermally bonded to form a seam.

4. The disposable applicator of claim 1 wherein said first inner layer is made of a fluid impervious material.

5. The disposable applicator of claim 1 wherein said first outer layer comprises absorbent fibers and substantially non-absorbent fibers.

6. The disposable applicator of claim 1 wherein said second outer comprises absorbent fibers and substantially non-absorbent fibers.

7. A disposable semi-enclosed applicator for distributing a substance onto a target surface, said applicator comprising:
(a) a first panel, said first panel comprising an inner layer, an outer layer and a reservoir positioned between said inner layer and said outer layer, wherein said reservoir is dispensible through said outer layer and wherein said outer layer comprises absorbent fibers and substantially non-absorbent fibers; and
(b) a second panel;
wherein said first panel and said second panel are attached to form a cavity in between and wherein said inner layer is made of a thermally bondable material.

8. A disposable semi-enclosed applicator for removing a substance from a target surface, said applicator comprising:
(a) a first panel; and
(b) a second panel, said second panel comprising an inner layer, an outer layer and an absorbent core positioned between said inner layer and said outer layer, wherein said inner layer is made of a thermally bondable material, wherein said outer layer comprises absorbent fibers and substantially non-absorbent fibers and
wherein said first panel and said second panel are attached to form a cavity in between.

9. A kit for distributing a substance onto a target surface, said kit comprising:
(a) a semi-enclosed applicator comprising:
(i) a first panel, said first panel comprising a first inner layer and a first outer layer; and
(ii) a second panel, said second panel comprising a second inner layer, a second outer layer and an absorbent core positioned between said second inner layer and said second outer layer, wherein said first panel and said second panel are attached to form a cavity in between and wherein said first inner layer is made of a thermally bondable material; and
(b) a reservoir containing a product.

10. A disposable applicator for distributing a substance onto a target surface, said applicator comprising:
a panel, said panel comprising an inner layer, an outer layer and a reservoir containing a product, said reservoir being positioned between said inner layer and said outer layer, wherein said reservoir is dispensible through said outer layer and wherein said outer layer comprises absorbent fibers and substantially non-absorbent fibers.

11. A disposable semi-enclosed applicator for distributing a substance onto a target surface, said applicator comprising:
(a) a first layer of a thermally bondable material, wherein said first layer comprises absorbent fibers and substantially non-absorbent fibers;
(b) a second layer of a thermally bondable material, wherein said first and second layers are thermally bonded to form a chassis having a cavity in between said first and second layers;
(c) at least a third layer of material attached to said first layer of thermally bondable material; and
(d) at least a fourth layer of material attached to said second layer of thermally bondable material.

12. The disposable applicator of claim 11 wherein said third layer of material is a porous material.

13. The disposable applicator of claim 12 further comprising an actuable reservoir located between said first layer of thermally bondable material and said third layer of porous material.

14. The disposable applicator of claim 13 wherein said second layer of material is made of a fluid impervious material.

15. A disposable applicator, said applicator comprising:
a panel, said panel comprising an inner layer wherein said inner layer is made of a thermally bondable material, an absorbent core and an outer layer wherein said outer layer comprises absorbent fibers and substantially non-absorbent fibers.

* * * * *